United States Patent

Bellhouse et al.

(10) Patent No.: US 6,685,669 B2
(45) Date of Patent: **\*Feb. 3, 2004**

(54) PARTICLE DELIVERY

(75) Inventors: Brian John Bellhouse, Oxfordshire (GB); John Bell, Oxfordshire (GB)

(73) Assignee: PowderJect Research Limited, Oxford (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,403
(22) PCT Filed: Dec. 21, 1995
(86) PCT No.: PCT/GB95/03016
§ 371 (c)(1), (2), (4) Date: Jun. 23, 1997
(87) PCT Pub. No.: WO96/20022
PCT Pub. Date: Jul. 4, 1996

(65) Prior Publication Data

US 2002/0004641 A1 Jan. 10, 2002

(30) Foreign Application Priority Data

Dec. 23, 1994 (GB) ............................................. 9426379

(51) Int. Cl.[7] .................................................. A61M 5/30
(52) U.S. Cl. ............................ 604/68; 604/70; 604/140
(58) Field of Search .......................... 604/68, 70, 140, 604/141, 143, 146

(56) References Cited

U.S. PATENT DOCUMENTS

| 3,308,818 A | * | 3/1967 | Rutkowski |
| 3,595,231 A | | 7/1971 | Pistor |
| 3,788,315 A | | 1/1974 | Laurens |

(List continued on next page.)

FOREIGN PATENT DOCUMENTS

| EP | 370571 | * | 5/1990 |
| EP | 0 406 778 A1 | | 1/1991 |
| EP | 0 469 814 A1 | | 2/1992 |
| FR | 2 360 031 | | 8/1978 |
| GB | 2 206 794 A | | 1/1989 |
| WO | WO 92/04439 | | 3/1992 |
| WO | WO 94/24263 | | 10/1994 |
| WO | WO 95/19799 | | 7/1995 |
| WO | WO 96/12513 | | 5/1996 |
| WO | WO 96/25190 | | 8/1996 |

OTHER PUBLICATIONS

Nabulsi et al. (1994) *Meas. Sci. Technol.* 5:267–274.

*Primary Examiner*—Manuel Mendez
(74) *Attorney, Agent, or Firm*—Foley & Lardner (57) ABSTRACT

A needleless syringe comprising a body containing a lumen, an upstream end of which is, or is arranged to be, connected to a source of gaseous pressure which can suddenly be released into the lumen; the downstream end of the lumen terminating behind a bistable diaphragm which is movable between an inverted position in which it presents outwardly of the body a concavity for containing particles of a therapeutic agent, and an everted, outwardly convex, position; the arrangement being such that, in use, when gas under pressure is released into the lumen, the diaphragm will snap over from its inverted to its everted position and catapult the particles outwardly.

30 Claims, 3 Drawing Sheets

U.S. PATENT DOCUMENTS

| | | |
|---|---|---|
| 4,596,556 A | 6/1986 | Morrow et al. |
| 691,709 A * | 9/1987 | Cohen .................. 128/667 |
| 4,945,050 A * | 7/1990 | Sanford et al. |
| 5,026,343 A | 6/1991 | Holzer |
| 5,049,125 A | 9/1991 | Accaries et al. |
| 5,062,830 A | 11/1991 | Dunlap |
| 5,149,655 A | 9/1992 | McCabe et al. |
| 5,204,253 A | 4/1993 | Sanford et al. |
| 5,282,785 A | 2/1994 | Shapland et al. |
| 5,330,446 A | 7/1994 | Weldon et al. |
| 5,371,015 A | 12/1994 | Sanford et al. |
| 5,630,796 A | 5/1997 | Bellhouse et al. |

* cited by examiner

PARTICLE DELIVERY

CROSS-REFERENCE TO RELATED APPLICATION

This application is a 371 of International Patent Application Number PCT/GB95/03016, filed Dec. 21, 1995, designating the United States, from which priority is claimed pursuant to 35 U.S.C. §365(c) and which is incorporated herein by reference in its entirety.

TECHNICAL FIELD

The present invention relates generally to a needleless syringe for use in delivery of particles comprising a therapeutic agent to a target surface. More particularly, the invention is drawn to a needleless syringe system configured for delivery of particles comprising a therapeutic agent from a first surface of a diaphragm using a force imparted upon a second surface of the diaphragm by a gas flow.

BACKGROUND OF THE INVENTION

In commonly owned U.S. Pat. No. 5,630,796, a noninvasive delivery system is described that entails the use of a needleless syringe. The syringe is used for transdermal delivery of powdered therapeutic compounds and compositions to skin, muscle, blood or lymph. The syringe can also be used in conjunction with surgery to deliver therapeutics to organ surfaces, solid tumors and/or to surgical cavities (e.g., tumor beds or cavities after tumor resection).

The needleless syringe is constructed as an elongate tubular nozzle, having a rupturable membrane initially closing the passage through the nozzle adjacent to the upstream end of the nozzle. Particles comprising a powdered therapeutic agent are located adjacent to the membrane. The therapeutic agent is delivered using an energizing means which applies a gaseous pressure to the upstream side of the membrane that is sufficient to burst the membrane, thereby producing a supersonic gas flow through the nozzle in which the particles are entrained.

As explained in U.S. Pat. No. 5,630,796, the particles comprising the therapeutic agent may be carrier particles coated, for example, with genetic material, or may be powdered therapeutic agents for all kinds of therapeutic use. With respect to delivery of powdered therapeutic agents per se, e.g., agents delivered without the aid of a carrier particle, general delivery parameters include a particle size preferably in the range of about 10–40 $\mu$m, a particle density preferably in the range of about 0.5–2.0 g/cm$^3$, and an initial velocity preferably in the range of about 200–2500 m/sec with a momentum density preferably in the range of 4–7 kg/sec/m.

SUMMARY OF THE INVENTION

In one embodiment of the invention, a needleless syringe is provided. The needleless syringe is capable of accelerating particles comprising a therapeutic agent across skin or mucosal tissue of a vertebrate subject. The syringe comprises, in operative combination, a body having a lumen extending therethrough. The lumen has an upstream terminus and a downstream terminus, and the upstream terminus of the lumen is interfaced with an energizing means such as a volume of a pressurized driving gas. The syringe further includes a diaphragm arranged adjacent to the downstream terminus of the lumen, wherein the diaphragm has an internal surface facing the lumen and an external surface facing outwardly from the syringe. The diaphragm is moveable between an initial position in which a concavity is provided on the external surface of the diaphragm, and a dynamic position in which the external surface of the diaphragm is substantially convex.

In certain aspects of the invention, the diaphragm is an eversible dome-shaped membrane that is comprised of a flexible polymeric material. In other aspects, the diaphragm is a bistable membrane that is moveable between an initial, inverted position and a dynamic, everted position. Particles comprising a therapeutic agent are generally housed within the concavity provided by the external surface of the diaphragm when in its initial position. The body of the needleless syringe can be configured as an elongate tubular structure with the diaphragm arranged over the downstream terminus of a lumen extending along the major axis of the tubular structure, or over an opening adjacent to the downstream terminus, which opening faces in a direction substantially perpendicular to the major axis of the tubular structure.

In another embodiment, a dome-shaped diaphragm for use with a needleless syringe is provided. The diaphragm has a concavity that sealably contains particles comprising a therapeutic agent.

In yet a further embodiment of the invention, a method for transdermal delivery of particles comprising a therapeutic agent is provided. The method entails providing a needleless syringe according to the invention, wherein the syringe has a diaphragm with a concave surface and a convex surface, and particles comprising the therapeutic agent are disposed on the concave surface of the diaphragm. A gaseous shock wave is released in a direction toward the convex surface of the diaphragm, wherein the shock wave provides sufficient motive force to impel the diaphragm to an everted position, thereby dislodging the particles from the diaphragm and accelerating them toward a target surface.

In certain aspects of the invention, the particles are accelerated toward the target surface in a direction substantially collinear with the direction of travel of the gaseous shock wave. In other aspects of the invention, the particles are accelerated toward the target surface in a direction transverse to the direction of travel of the gaseous shock wave.

These and other embodiments of the present invention will readily occur to those of ordinary skill in the art in view of the disclosure herein.

BRIEF DESCRIPTION OF THE FIGURES

Some examples of syringes constructed in accordance with the present invention are illustrated in the accompanying drawings, in which.

DETAILED DESCRIPTION OF THE PREFERRED EMBODIMENTS

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a therapeutic agent" includes a mixture of two or more such agents, reference to "a gas" includes mixtures of two or more gases, and the like.

A. Definitions

Unless defined otherwise, all technical and scientific terms used herein have the same meaning as commonly understood by one of ordinary skill in the art to which the invention pertains. The following terms are intended to be defined as indicated below.

The term "transdermal", delivery captures both transdermal (or "percutaneous") and transmucosal administration, i.e., delivery by passage of a therapeutic agent through the skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs, Vols.* 1–3, Kydonieus and Berner (eds.), CRC Press, (1987). Aspects of the invention which are described herein in the context of "transdermal" delivery, unless otherwise specified, are meant to apply to both transdermal and transmucosal delivery. That is, the compositions, systems, and methods of the invention, unless explicitly stated otherwise, should be presumed to be equally applicable to transdermal and transmucosal modes of delivery.

As used herein, the terms "therapeutic agent" and/or "particles of a therapeutic agent" intend any compound or composition of matter which, when administered to an organism (human or nonhuman animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antimigrane agents; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), erodible polymers (such as polylactic acid, polyglycolic acid, and copolymers thereof), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

"Gene delivery" refers to methods or systems for reliably inserting foreign nucleotide sequences, either DNA or RNA, into a recipient's cells. Such methods can result in expression of non-integrated transferred nucleotide sequences, extrachromosomal replication and expression of transferred replicons (e.g., episomes), or integration of transferred genetic material into the genomic DNA of the recipient's cells.

By "vector" is meant any genetic element, such as a plasmid, phage, transposon, cosmid, chromosome, virus, virion, etc., which is capable of replication when associated with the proper control elements and which can transfer gene sequences between cells.

B. General Methods

In one embodiment of the invention, a needleless syringe is provided having a body containing a lumen. An upstream end of the lumen is, or is arranged to be, connected to a source of gaseous pressure which can suddenly be released into the lumen. The downstream end of the lumen terminates behind an eversible diaphragm which is movable between an inverted position which provides a concavity for containing particles comprising a therapeutic agent, and an everted, outwardly convex, position. The eversible diaphragm is arranged such that, when an energizing gas flow is released into the lumen, the diaphragm will travel from its inverted to its everted position, thereby projecting the particles from the diaphragm toward a target surface.

One advantage provided by the present invention is that even when a supersonic gaseous shockwave is used as the energizing means to snap the diaphragm over from its inverted to its everted position, the diaphragm contains the gas within the lumen, preventing contact of the gas stream with the target surface. Therefore, unlike prior devices, no provision has to be made for dissipating and/or silencing a gaseous shockwave reflected from the target. Also the target surface is not subjected to the possibility of trauma or mechanical harm from the high speed gas flow.

A number of suitable energizing means can be used with the present needleless syringe device. For example, a chamber containing a reservoir of compressed gas can be arranged at the upstream end of the lumen. The gas can be released from the energizing chamber by way of a pierceable membrane or a valve, such as a spring-loaded ball valve, which is actuated by either mechanical means or by manual manipulation, for example, by movement of two parts of the syringe relative to each other. Alternatively, the energizing chamber can be fitted with means for providing a controlled build-up of gaseous pressure from an upstream or associated source. For example, release of a pressurized gas flow may be achieved by building up pressure behind a rupturable membrane until the pressure difference across the membrane is sufficient to rupture the membrane and release the gas suddenly into the lumen. The velocity of the shockwave provided by the energizing means can be increased if the driving gas is lighter than air, e.g., helium. This effect can be enhanced if the lumen is initially filled with a gas which also is lighter than air, e.g., helium.

In order to avoid loss of particles and/or to maintain sterility of the particles prior to delivery, the concavity can be covered, for example, by a retractable shield or a thin barrier film which is readily penetrated by the particles upon delivery.

Figure 1:
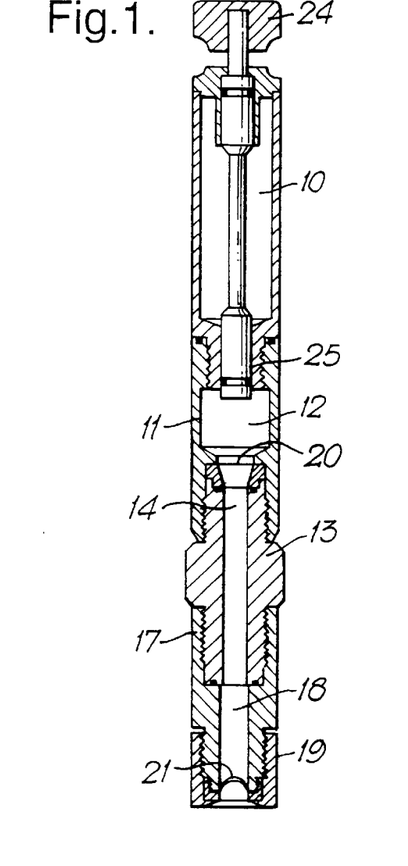
FIG. 1 is an axial section through a first embodiment of the invention.
Figure 2:
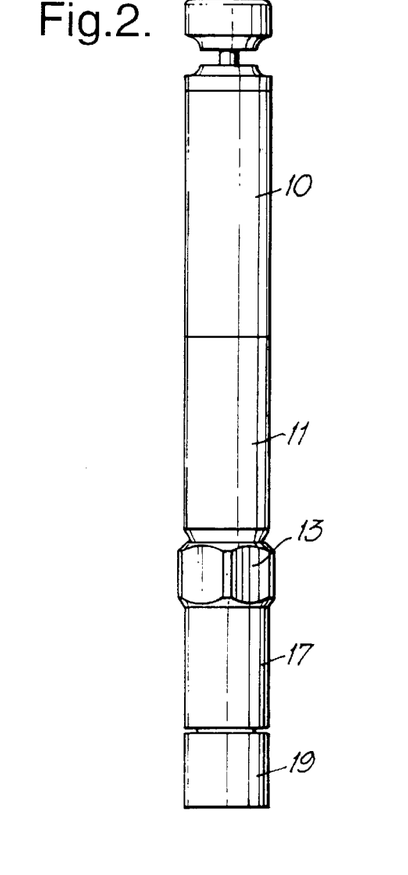
FIG. 2 is a side elevational view of the embodiment of FIG. 1.
Figure 3:
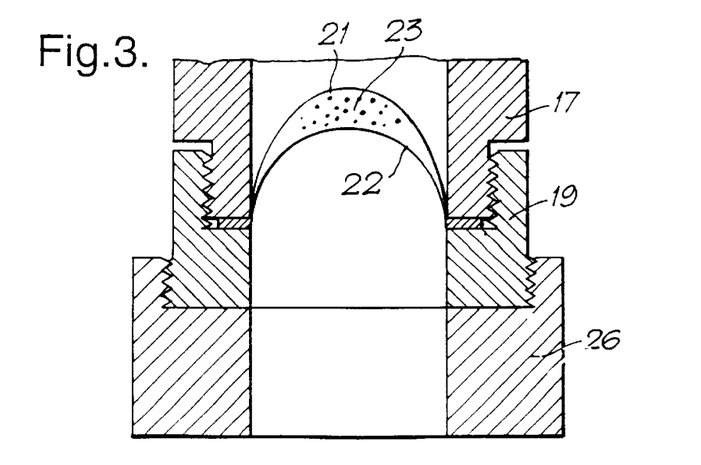
FIG. 3 is an axial section of a portion of the embodiment of FIG. 1.

Referring now to the accompanying drawings, FIGS. 1–3 show one embodiment of a needleless syringe suitable for transdermal delivery of particles comprising a therapeutic agent. As particularly shown in FIGS. 1 and 2, the syringe has an energizing means comprised of a cylindrical reservoir 10 initially containing helium under a pressure of about 80 bar. The reservoir 10 is sealably coupled to, and in fluid communication with, a first opening of tubular body portion 11 which contains a rupture chamber, indicated at 12. Connection of the reservoir to the tubular body portion can be facilitated by any suitable pressure-tight coupling. A second opening of the body portion 11 is sealably coupled to, and in fluid communication with, a second tubular body portion 13 having a passageway 14 which extends therethrough. The passageway 14 comprises an upstream terminus which interfaces with the rupture chamber 12, and a downstream terminus which interfaces with a third tubular body portion 17 when the body portion 13 is sealably coupled to the body portion 17 also by way of a pressure-tight coupler. The tubular body portion 17 contains a passageway 18, and has a tubular tip portion 19 attached thereto. The passageways 14 and 18 establish a lumen through which gasses released from the rupture chamber 12 may pass.

The particular construction of the syringe of FIGS. 1 and 2 allows the reservoir 10 to be stored separately and fitted to the rest of the syringe immediately prior to use. The body portions 11 and 13 are readily separable to allow the sandwiching between them of an optional rupturable membrane 20. The tip portion 19 is separable from the body portion 17 to allow the sandwiching between them of a diaphragm 21 which has an internal surface facing the lumen provided by the passageways 14 and 18, and an external surface facing outwardly relative to the syringe. The diaphragm 21 is moveable between an initial position in which a concavity is provided on the external surface of the diaphragm, and a dynamic position in which the external surface of the diaphragm is substantially convex. The body portions 13 and 17 are also readily separable such that one or more of the syringe components 17, 19 and 21 can be provided as a disposable unit.

Particles comprising a therapeutic agent will initially be provided in the concavity provided by the outwardly facing external surface of the diaphragm 21. The particles may be attached to the diaphragm by electrostatic forces, by their natural sticky nature, or by way of an adhesive agent such as trehalose or silicone oil, or by the adhesive effect provided by evaporation of water or ethanol in which the particles have been suspended. Alternatively, the particles may be attached to the diaphragm by way of compacting the particles within the concavity of the diaphragm using a suitable press. The diaphragm 21 may, optionally, further comprise features on the concave side thereof, which features are useful for retaining the particles. For example, one or more annular rings, or a centrally disposed recess can be provided respectively on, or in, the external surface of the diaphragm.

Referring to FIG. 3, in the interest of sterility and/or of maintaining the integrity of the therapeutic agent, the diaphragm 21 can be covered and sealed at its edge to a penetratable membrane such as a weak barrier film 22 to form a sealed capsule containing the therapeutic agent particles 23. The weak barrier film 22 may further contain lines of weakness provided by a cut or score in the barrier to assist rupture and reduce membrane fragmentation.

The diaphragm 21 can be an eversible dome-shaped membrane that is comprised of any suitably resilient, flexible polymeric material which can withstand the impact of a shock wave provided by a gas flow travelling at a velocity approaching supersonic speed. Exemplary materials include, for example, a polyurethane or silicone rubber material. Selection of suitable flexible dome-shaped membranes is within the capabilities of the reasonably skilled artisan upon reading this specification, wherein the flexibility of an eversible dome can be characterized by the static buckling stress provided by a particular membrane material of a given thickness. For example, the static buckling stress of a representative membrane can be determined by connecting the membrane to a high-pressure cylinder, and gradually applying increasing pressure to the convex face thereof such that the differential pressure at which the dome first begins to buckle ($P_B$) can be noted. The buckling pressure ($P_B$), then, represents the difference in pressure between the convex and concave faces at the point of buckling. The static buckling stress ($\sigma_B$) can be related to the buckling pressure ($P_B$), the effective dome radius (r), and the wall thickness (t) of the membrane, using the relationship: $\sigma_B = P_B(r)/2t$.

The buckling stress ($\sigma_B$) of a given dome-shaped membrane is strongly dependent on the dome material, but only weakly dependent on the radius (r), wall thickness (t) and the overall dome shape. A highly flexible dome-shaped membrane can be characterized by a buckling stress ($\sigma_B$) on the order of unity when measured in units of $N/mm^2$. In this regard, the measured buckling stress of a polyurethane dome membrane suitable for use in the device of the present invention is around 0.75 N/mm$^2$, whereas a substantially rigid, inelastic dome comprised of a polyester film such as Mylar® typically has a buckling stress of at least about 23 N/mm$^2$.

Figure 8:
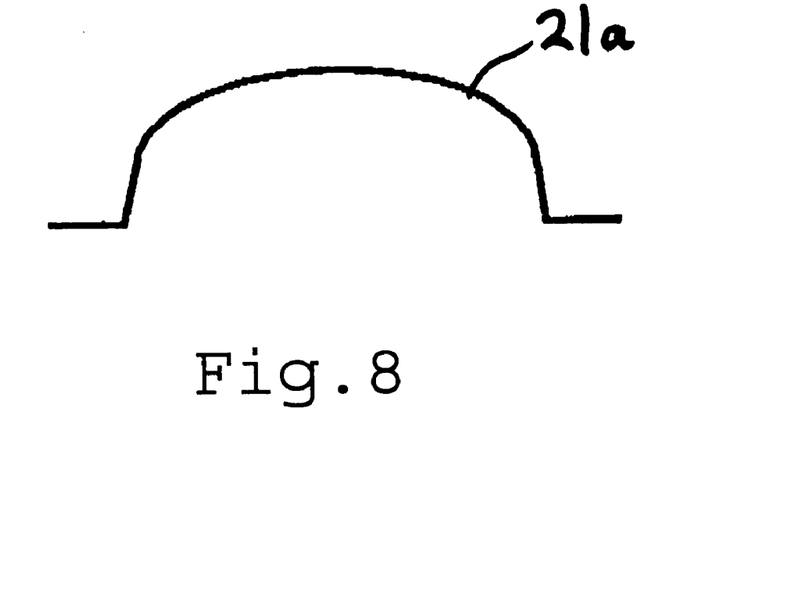
FIG. 8 is a side view of a plateau-shaped diaphragm.
Figure 9:
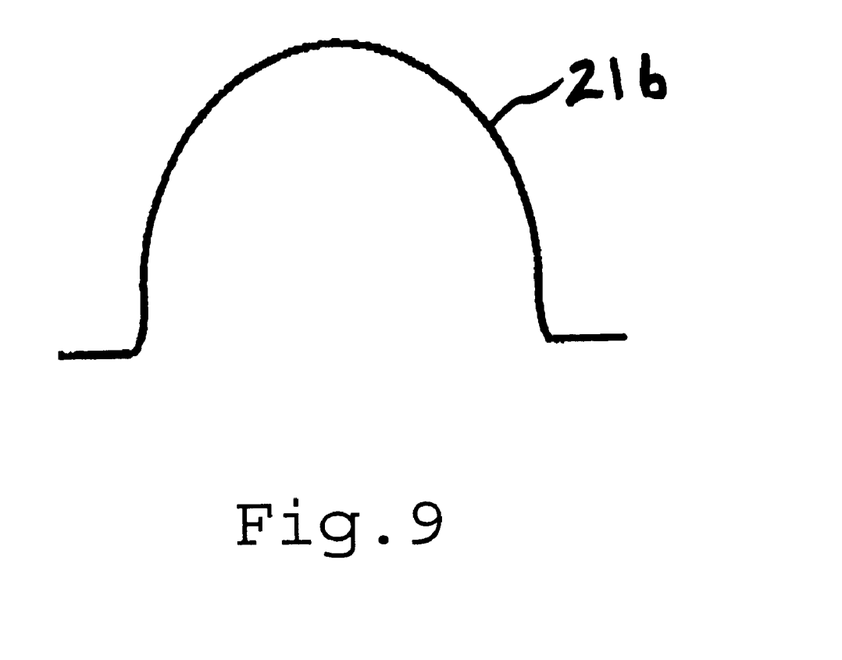
FIG. 9 is a side view of a dome-shaped diaphragm.

Flexible dome-shaped membranes used in connection with the present invention can have a number of suitable geometries, wherein the mode of dome eversion can be closely related to the geometry of the dome. Two common modes of dome eversion include (i) eversion starting at the center (axis of radial symmetry) of the dome and (ii) eversion starting at the maximum radius of the dome. Referring now to FIGS. 8 and 9, two exemplary dome geometries are depicted. The dome 21*a* of FIG. 8 is a plateau-shaped dome, and the dome 21*b* of FIG. 9 is a conventionally shaped dome. The plateau-shaped dome of FIG. 8 generally everts at a higher static buckling stress than the dome of FIG. 9.

The mode of dome eversion provided by an eversible dome-shaped membrane can be used to tailor delivery parameters, such as the size of the target area receiving the particles comprising the therapeutic agent, and the uniformity of particle penetration into a target surface. In this regard, a plateau-shaped dome used under the same conditions as a conventional dome generally provides a more even penetration of particles that are dispersed over a wider target area. Conversely, a conventionally shaped dome can be used to concentrate particle delivery into a narrow, central region in which particle penetration is greatest at the axis of radial symmetry, subsiding radially outward therefrom.

Alternatively, the diaphragm 21 can be a bistable membrane which is shaped in the form of a dome comprised of a resilient, polymeric material such as polyester (e.g., Mylar®). The bistable membrane can be formed by thermoforming in a suitable jig. The bistable membrane is moveable between an initial inverted position and a dynamic everted position.

In use, the needleless syringe of FIGS. 1 and 2 is assembled to provide suitable pressure-tight fittings between the components, and the lumen provided by passageways 14 and 18 is prefilled with helium at approximately atmospheric pressure. The tip 19 is placed in proximity to, or in contact with, the target skin or mucosal surface to be treated, and a plunger 24 is depressed to actuate a valve 25 to an open position which allows the pressurized helium to be discharged from the reservoir 10 and pass into the rupture chamber 12. The valve 25 may preferably be configured such that the frontal area of the plunger is greater at the downstream exit of the cylindrical reservoir 10 relative to the upstream frontal area of the plunger, resulting in a self-opening (and quick-opening) valve. When the pressure in the rupture chamber 12 has reached a sufficient value of, for example, about 23 bar, the rupture membrane 20 bursts, releasing a gaseous shockwave which propagates through the lumen formed by the passageways 14 and 18 and contacts the internal surface of the diaphragm 21. The impact of the gaseous shock wave upon the internal surface of the diaphragm provides sufficient force to suddenly impel the diaphragm from its initial position to a dynamic everted (outwardly convex) position, thereby dislodging the particles comprising the therapeutic agent from the external surface of the diaphragm and propel them toward a target surface, simultaneously rupturing the barrier film 22. The particles are accelerated from the diaphragm at velocities sufficient for the transdermal delivery thereof across skin or mucosal tissue.

In an optional device configuration, as depicted in FIG. 3, a short tubular spacer 26 may be provided to increase the distance between the tip portion 19 and a target surface. The spacer helps reduce the velocity of the particles before impact with the target surface, and enables the particles to become more spread out in order to increase the target area.

One important feature of the needleless syringe design concerns means to control the static pressure retained within the device subsequent to particle delivery. A large build-up of static pressure can be detrimental to the operability of the device when highly flexible dome-shaped membranes are employed. Thus, it is preferable that static pressure build-up is minimized or substantially eliminated. A direct way in which to minimize static pressure build-up is to increase the ratio of lumen volume-to-gas canister volume. Static pressure can also be substantially eliminated by venting the lumen to atmosphere. In this regard, such venting surprisingly does not inhibit the effectiveness of particle delivery that is attainable from the device, since the propagation of a shock wave is the key element in the eversion of the diaphragm. Thus, a vent that is substantially perpendicular with the major axis of the lumen, and having a diameter of less than half that of the lumen, is sufficient to release a driving gas after eversion of the diaphragm while not inhibiting the travel or the strength of the gaseous shock wave. Furthermore, vents arranged adjacent to the diaphragm, for example in the body part 17 or the downstream portion of body part 13, can improve the delivery performance of the needleless syringe.

Another design consideration relates to the generation of the shock wave within the needleless syringe device. For example, one way to produce a controlled shock wave is to burst a uniform rupture membrane within the syringe to release the driving gas. Rupture membranes comprised of polyester films (e.g., Mylar®) having a thickness of about 12–50 μm are adequate for these purposes. The rupture membrane initially closes-off the downstream opening of the rupture chamber 12, and a shock wave is generated once the driving gas (that has been released from the reservoir 10 or from a gas canister) reaches a critical burst pressure within the rupture chamber sufficient to rupture the membrane and allow passage of the gaseous shock wave into the lumen. Delivery performance can be optimized by increasing the rupture membrane burst pressure and/or by increasing the volume of the rupture chamber. Increases in the rupture membrane burst pressure, e.g., by increasing the thickness of a given diameter rupture membrane, provide a larger step change in pressure across the shock wave. Increased rupture chamber volume provides a concomitant increase in the mass flow, which sustains the supersonic transients of the shock wave. In order to provide sufficient mass flow through the device, the volume of the rupture chamber 12 can be substantially the same as the volume of the reservoir 10 or the volume of a gas canister.

In the device depicted in FIGS. 1 and 2, the body of the needleless syringe is configured as an elongate tubular structure, wherein the diaphragm 21 is arranged over, and closes the downstream terminus of the lumen formed by passageways 14 and 18. Upon release, the gaseous shock wave travels down the lumen and impacts the interior surface of the diaphragm, causing the acceleration of particles retained on the exterior surface of the diaphragm toward a target surface in a direction that is substantially collinear with the direction of travel of the gaseous shock wave.

In an alternative embodiment of the invention, a needleless syringe is provided which is capable of accelerating particles comprising a therapeutic agent toward a target surface in a direction transverse to the direction of travel of a gaseous shock wave. Referring now to FIGS. 4 to 7, one such device is depicted which comprises an arterial catheter and is useful for treatment of vascular proliferative disorders.

Figure 4:
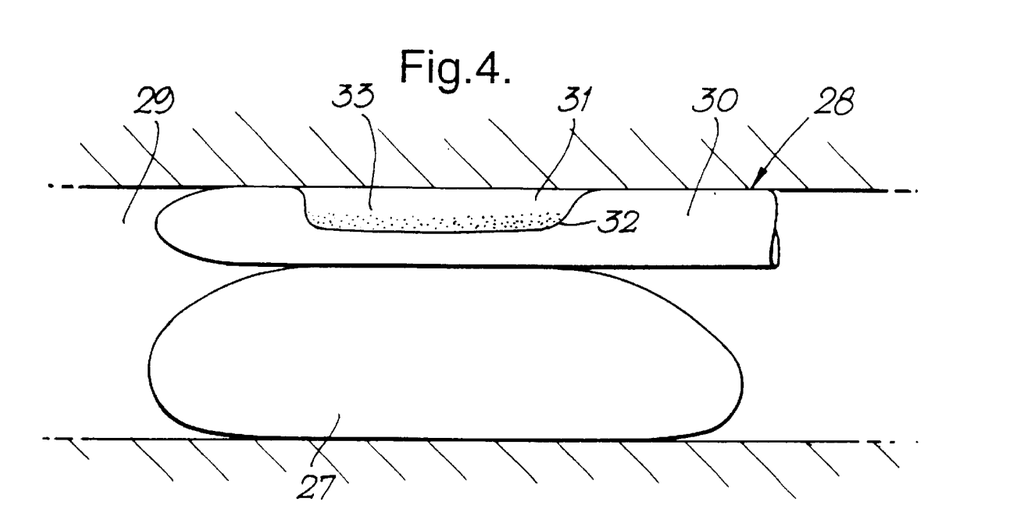
FIG. 4 is a pictorial representation of a further embodiment of the invention comprising a catheter and a positioning means.
Figure 5:
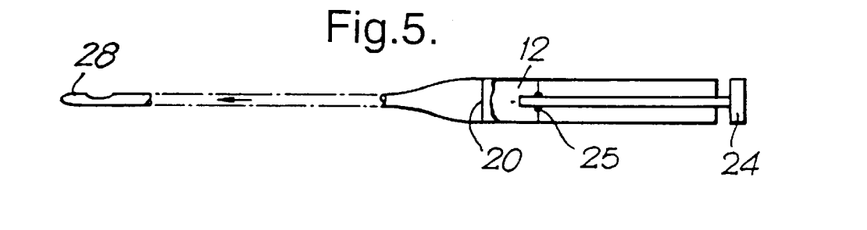
FIG. 5 is a pictorial representation of the embodiment of FIG. 4.
Figure 6:
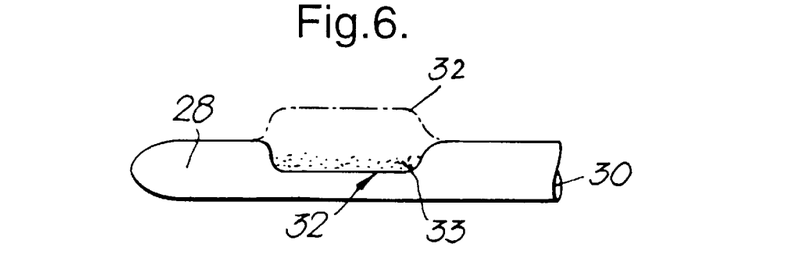
FIG. 6 is a plan side view of the tip of the embodiment of FIG. 4 showing the diaphragm in two different positions.

As seen in FIG. 5, a catheter is provided having at its upstream end a reservoir containing a driving gas. Release of the driving gas from the reservoir is controlled by actuation of a valve 25'. The released gas passes into a rupture chamber 12' having a rupturable membrane 20' similar to the device described herein above. The catheter may be configured as a triple lumen catheter, wherein one lumen provides the usual guidewire, the second carries gas to inflate a positional balloon 27 for urging a body 28 adjacent to the leading end (shown in FIG. 4) of the catheter against a wall of an artery 29, and the third lumen 30 is used to propagate a gaseous shockwave to the tip of the catheter.

Figure 7:
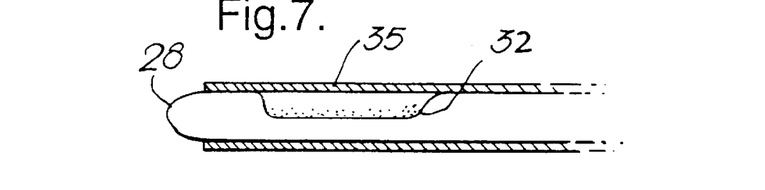
FIG. 7 is an axial section of a further embodiment of the invention.

At an opening 31 in a sidewall of the catheter body 28, there is provided a diaphragm 32 that can be comprised of an eversible, dome-shaped flexible membrane, or a bistable membrane as described above. When the diaphragm 32 is in an initial position as depicted in FIG. 4 and in solid lines in FIG. 6, the diaphragm provides a concavity in which particles 33 comprising a therapeutic agent, e.g., containing or consisting of DNA, are located. In order to avoid unwanted loss of the particles from concavity by means of the blood flow in the artery, the cavity may initially be covered by a barrier film or by a retractable sleeve 35 as shown in FIG. 7.

The catheter is used analogously to the syringe of FIGS. 1 and 2. Thus release of a driving gas from the reservoir into the rupture chamber eventually bursts the rupture membrane and causes a shockwave to be propagated along the lumen 30, causing the diaphragm 32 to travel suddenly to a dynamic, everted position as depicted in broken lines in FIG. 6, thereby propelling the particles 33 outwardly in a direction transverse to the direction of travel of the gaseous shock wave, and toward the wall of the artery 29.

Alternatively, it may be desirable for the diaphragm 32 to be housed within the peripheral envelope of the catheter body, not only when in its initial, inverted position in order to avoid interference during insertion of the catheter, but also when in its dynamic, everted position to avoid the possibility of a damaging impact with the arterial wall.

This particular embodiment of the invention is particularly useful the treatment of vascular proliferative diseases, such as for delivering genetic material into the wall of the expanded stenotic blood vessel to transform endothelial cells lining the wall of the blood vessel, and thereby preventing subsequent restenosis/re-occlusion of the blood vessel.

Moreover, the catheter-based delivery system may find other uses, for example in the localised delivery of a combination of compounds (e.g., for chemotherapy) to specific internal organs, or for local organ-based hormone replacement. The catheter device is also useful in the administration of drugs or DNA to accessible surfaces for medical purposes, for example in the treatment of tumours of mucosal surfaces, such as respiratory, gastrointestinal or genito-urinary tracts.

With respect to both of the above-described needleless syringe devices, the gas provided by the energizing means may be helium at a pressure of about 40 to 80 bar. However, any other suitable delivery gas may be used.

The needleless syringes of the present invention can be used for transdermal delivery of powdered therapeutic compounds and compositions, for delivery of genetic material into living cells (e.g., gene therapy or nucleic acid vaccination), both in vivo and ex vivo, and for the delivery of biopharmaceuticals to skin, muscle, blood or lymph. The syringes can also be used in conjunction with surgery to deliver therapeutic agents, drugs, immunogens, and/or biologics to organ surfaces, solid tumors and/or to surgical cavities (e.g., tumor beds or cavities after tumor resection). In theory, practically any agent that can be prepared in a substantially solid, particulate form can be safely and easily delivered using the present devices.

Delivery of therapeutic agents from the above-described needleless syringe systems is generally practiced using particles having an approximate size generally ranging from 0.1 to 250 μm. For drug delivery, the optimal particle size is usually at least about 10 to 15 μm (the size of a typical cell). For gene delivery, the optimal particle size is generally substantially smaller than 10 μm. Particles larger than about 250 μm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin or mucosal tissue. In this regard, optimal particle densities for use in needleless injection generally range between about 0.1 and 25 g/cm$^3$, preferably between about 0.9 and 1.5 g/cm$^3$, and injection velocities can range from about 200 to about 3,000 m/sec.

When nucleic acid preparations, e.g., DNA molecules, are to be delivered using the devices of the present invention, the preparations may optionally be encapsulated, adsorbed to, or associated with, carrier particles. Suitable carrier particles can be comprised of any high density, biologically inert material. Dense materials are preferred in order to provide particles that can be readily accelerated toward a target over a short distance, wherein the particles are still sufficiently small in size relative to the cells into which they are to be delivered.

In particular, tungsten, gold, platinum and iridium carrier particles can be used. Tungsten and gold particles are preferred. Tungsten particles are readily available in average sizes of 0.5 to 2.0 μm in diameter, and are thus suited for intracellular delivery. Gold is a preferred material since it has high density, is relatively inert to biological materials and resists oxidation, and is readily available in the form of spheres having an average diameter of from about 0.2 to 3 μm.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Transmucosal Delivery of Testosterone

Testosterone and its derivatives have been given orally for the treatment of hypogonadal men (Niesschlag et al. (1976) *Hormone Research* 7:138–145; Skakkebaek et al. (1981) *Clinical Endocrinol.* 14:49–61; and Gooren, L. (1986) *Intern, J. Androl.* 9:21–26). The "first-pass" effect limits the effectiveness of testosterone treatment when administered orally, where the testosterone is absorbed entering the hepatic circulation and immediately degraded by the liver (98% first pass degradation). Moreover, a major drawback of oral androgenic therapy compared to parenteral treatment is the exposure of the liver to high androgen loads, increasing the likelihood of undesirable effects on, for example, lipid metabolism (Conway et al., (1988) *Int. J. Androl.* 112:47–64; and Thompson et al., (1989) *JAMA* 261:1165–1168).

Thus, the following study was carried out to assess the transmucosal delivery of testosterone using a needleless syringe constructed in accordance with the present invention.

Testosterone (Sigma Chemicals) was milled and sieved into a particle size range (approximately 50–100 µm) suitable for transmucosal delivery from a needleless syringe using standard stainless steel mesh sieves. Female New Zealand White rabbit subjects weighing between 2.2–2.8 kg were used and allowed food and water ad libitum. The rabbits (n=8) were randomly assigned to one of two treatment groups. The first treatment group received testosterone (2.0 mg dose) as a suspension in 35% polyvinylpyrrolidone C-30 in water (6 mg/g testosterone concentration) via subcutaneous injection. The second treatment group received testosterone (2.0 mg dose of testosterone particles ranging from 53–75 µm) as two 1.0 mg transmucosal administrations from an OralJect™ needleless syringe device abutted against the cheek mucosa.

Whole blood (1.0 ml) was taken at times 0, 0.5, 1, 2, 4, 6, 8, 12, 24 and 48 hours, the serum aspirated and assayed for testosterone by radioimmunoassay (DPC). The OralJect™ device is a prototype device of the present invention that is actuated by helium at 40 bar.

The results of the study are depicted below in Table 1 which shows the mean results and ranges for each treatment group from the study. As can be seen, testosterone bioavailability in the order of 48.3% was achieved following OralJect™ transmucosal delivery with a $t_{max}$ of 30 minutes in all animals. $C_{max}$ (the mean maximum serum concentration) was not significantly different between treatments although there was a tendency for it to be lower following OralJect™ administration. A second minor peak of serum testosterone was evident at 12 hours post administration suggesting a possible depot effect following transmucosal delivery of testosterone by the OralJect™ device.

TABLE 1

| Treatment | Subcutaneous | OralJect ™ |
|---|---|---|
| $C_{max}$ nmol/I | 34.8 ± 6.9 | 25.5 ± 3.5 |
| $C_{max}$ range nmol/I | 26.9–55.2 | 177–33.5 |
| % BA† | NA | 48.3 |

†% bioavailability

These data demonstrate that it is possible to deliver a hydrophobic drug such as testosterone transmucosally using the device of the present invention. The pharmacokinetic profile observed for such delivery was markedly different from that achieved following subcutaneous administration of the same formulation of testosterone.

EXAMPLE 2

Delivery of a Powdered Local Anaesthetic to Oral Mucosa using a Needleless Syringe Device The following studies were carried out to assess the effectiveness of transmucosal delivery to oral mucosa using a device constructed in accordance with the present invention, to provide a comparison between such delivery and a conventional needle-syringe injection, and to assess the anaesthetic effect provided by transmucosal delivery.

A randomized, double-blind, negatively controlled study was carried out in normal, healthy human subjects as follows. Initially, a single 3 mg dose of lignocaine HCL particles sized between 38 and 53 µm was delivered from a needleless syringe constructed in accordance with the invention. The lignocaine was delivered to the oral mucosa adjacent to the number 12 and 22 lateral incisors in 14 trial subjects. The delivery sites were then visually assessed for evidence of damage or irritation to the mucosal tissues. In all subjects, no evidence of any tissue reaction was observed 24–48 hours after delivery.

In a second study, a single 3.0 mg dose of lignocaine HCL particles (as above) was delivered using a needleless syringe, and a single 0.2 mL dose of 2% lignocaine HCL was delivered via needle-syringe injection. Pain associated with the administration of each treatment was scored in all 14 subjects using a 100 mm visual analogue scale immediately after each treatment, wherein 100% indicates a painful treatment, and 0% indicates a pain-free treatment. The needleless syringe employed in the study was operated using 40 bar helium driving gas to expel anaesthetic particles from a flexible, eversible dome-shaped membrane comprised of a 400 µm, 6 mm polyurethane film. The mean values of all 14 scores were: 2.4% for the needleless syringe-based procedure, and 49.9% for the needle-syringe injection, indicating that the delivery methods of the present invention are virtually painless relative to conventional injection techniques.

A randomized, double-blind study was then carried out as follows. Treatments were given to 14 subjects over the course of three visits. The treatments provided to the subjects in each visit were either a single 3.0 mg dose of Lignocaine HCL particles from the above-described needleless syringe device, or 0.0 mg (as a blinded negative control). Accordingly, treatments provided over the course of is the three visits were either: two actual (3.0 mg) doses of the anaesthetic particles and one placebo; or two placebos and one actual (3.0 mg) dose. Pain stimulus was provided by probing oral mucosa with the back of a 27G dental needle, wherein the probe sequence was a probe on an untreated area of the mucosa, and then a probe on the treated area of the mucosa 1 minute post delivery. Again, the pain associated with the probe of the untreated and treated areas was scored on visual analogue scales using the above scoring methods immediately after each probe.

The mean values of all pain response scores were: 55.6% for the control (untreated) probe; 30.6% for the placebo treated probe; and 15.0% for the actual treated probe. These results demonstrate a superior level of local anaesthesia relative to the placebo treatments.

Accordingly, novel needleless syringe delivery systems and methods for using the same are disclosed. Although preferred embodiments of the subject invention have been described in some detail, it is understood that obvious variations can be made without departing from the spirit and the scope of the invention as defined by the appended claims.

We claim:

1. A needleless syringe capable of accelerating particles comprising a therapeutic agent across skin or mucosal tissue of a vertebrate subject, said syringe comprising:

(a) a body having a lumen therein, wherein said lumen has an upstream terminus and a downstream terminus and the upstream terminus of the lumen is capable of interfacing with an energizing means; and (b) a diaphragm arranged adjacent to the downstream terminus of the lumen, said diaphragm having an internal surface facing the lumen and an external surface, wherein said diaphragm is moveable between an initial position in which a concavity is provided for said particles on the external surface of the diaphragm, and a dynamic position in which the external surface of the diaphragm is substantially convex.

2. The needleless syringe of claim 1, wherein the diaphragm is an eversible dome-shaped membrane comprised of a flexible polymeric material.

3. The needleless syringe of claim 2, wherein the flexible polymeric material is a polyurethane or a silicone rubber.

4. The needleless syringe of claim 1, wherein the diaphragm is a bistable membrane that is moveable between an initial inverted position and a dynamic everted position.

5. The needleless syringe of claim 1 further comprising a rupture chamber having a first opening adapted to interface with an energizing means, and a second opening which is in fluid communication with the upstream terminus of the lumen.

6. The needleless syringe of claim 5, wherein the second opening of the rupture chamber is closed by a rupturable membrane.

7. The needleless syringe of claim 1, wherein the upstream terminus of the lumen is interfaced with a source of pressurized gas.

8. The needleless syringe of claim 6, wherein the first opening of the rupture chamber is interfaced with a source of pressurized gas.

9. The needleless syringe of claim 7, wherein the source of pressurized gas comprises a gas canister containing a releasable volume of a driving gas.

10. The needleless syringe of claim 9 further comprising valve means capable of actuation to release a volume of the pressurized gas from the canister and thereby create a gaseous shock wave within the lumen.

11. The needleless syringe of claim 10, wherein the valve means comprises a rupturable membrane arranged over the upstream terminus of the lumen.

12. The needleless syringe of claim 10, wherein the valve means comprises a frangible covering arranged over an opening in the gas canister.

13. The needleless syringe of claim 8, wherein the source of pressurized gas comprises a gas canister containing a releasable volume of a driving gas.

14. The needleless syringe of claim 13, wherein the gas canister and the rupture chamber have substantially the same volume.

15. The needleless syringe of claim 1, wherein the lumen further contains a volume of a gas which is lighter than air.

16. The needleless syringe of claim 9, wherein the driving gas is comprised of helium.

17. The needleless syringe of claim 1 further comprising particles comprising a therapeutic agent housed within the concavity in the external surface of the diaphragm.

18. The needleless syringe of claim 17, wherein the particles are disposed between the external surface of the diaphragm and a retractable shield.

19. The needleless syringe of claim 17, wherein the particles are disposed between the external surface of the diaphragm and a penetratable membrane.

20. The needleless syringe of claim 17, wherein the particles are retained on the external surface of the diaphragm by an adhesive agent.

21. The needleless syringe of claim 20, wherein the adhesive agent is selected from the group consisting of trehalose and silicone oil.

22. The needleless syringe of claim 1, wherein the body comprises an elongate tubular structure and the diaphragm is arranged over the downstream terminus of the lumen.

23. The needleless syringe of claim 1, wherein the body comprises an elongate tubular structure and the diaphragm is arranged over an opening adjacent to the downstream terminus of the lumen, said opening facing in a direction substantially perpendicular to the major axis of the lumen.

24. A dome-shaped diaphragm for use with a needleless syringe, said diaphragm having a concavity sealably containing particles comprising a therapeutic agent.

25. A method for transdermally delivering particles comprising a therapeutic agent from a needleless syringe, said method comprising:

(a) providing a needleless syringe having an eversible diaphragm with a convex surface and a concave surface, wherein particles comprising the therapeutic agent are disposed on the concave surface of the diaphragm; and (b) releasing a gaseous shock wave in a direction toward the convex surface of the diaphragm with sufficient force to impel said diaphragm to an everted position, thereby dislodging the particles from the diaphragm and accelerating them toward a target surface.

26. The method of claim 25, wherein the particles are accelerated toward a target mucosal surface.

27. The method of claim 25, wherein the particles are accelerated toward the target surface in a direction substantially collinear with the direction of travel of the gaseous shock wave.

28. The method of claim 25, wherein the particles are accelerated toward the target surface in a direction transverse to the direction of travel of the gaseous shock wave.

29. The method of claim 25, wherein the diaphragm is a dome-shaped membrane comprised of a flexible polymeric material.

30. The method of claim 25, wherein the diaphragm is a bistable membrane that is moveable between an initial inverted position and a dynamic everted position.

* * * * *